(12) United States Patent
Crombez et al.

(10) Patent No.: US 8,318,234 B2
(45) Date of Patent: Nov. 27, 2012

(54) MIXED AQUEOUS SOLUTION OF L-LYSINE AND L-THREONINE AND METHOD OF PREPARING SAME

(75) Inventors: Mathilde Crombez, Amiens Cedex (FR); François Lefebvre, Amiens Cedex (FR); Takehiko Chikamori, Amiens Cedex (FR); Loïc Le Tutour, Amiens Cedex (FR); Yasuhiko Toride, Amiens Cedex (FR); Ichiro Fuke, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 94 days.

(21) Appl. No.: 12/870,294

(22) Filed: Aug. 27, 2010

(65) Prior Publication Data

US 2011/0045162 A1  Feb. 24, 2011

Related U.S. Application Data

(63) Continuation of application No. PCT/EP2009/052259, filed on Feb. 26, 2009, and a continuation of application No. PCT/IB2008/001889, filed on Feb. 29, 2008.

(51) Int. Cl.
  *A23L 1/305* (2006.01)
(52) U.S. Cl. .................. 426/648; 426/656; 426/807
(58) Field of Classification Search .................. 426/648, 426/656, 807
  See application file for complete search history.

(56) References Cited

U.S. PATENT DOCUMENTS

| | | | |
|---|---|---|---|
| 3,726,805 A * | 4/1973 | Maekawa et al. | 427/213.3 |
| 4,379,177 A | 4/1983 | McCoy et al. | |
| 4,919,945 A | 4/1990 | Spindler et al. | |
| 5,756,761 A | 5/1998 | Dueppen et al. | |
| 5,795,585 A | 8/1998 | Ikeda et al. | |
| 6,162,442 A | 12/2000 | Lotter et al. | |
| 6,329,548 B1 | 12/2001 | Hasegawa et al. | |
| 6,468,580 B1 | 10/2002 | Choi et al. | |
| 6,800,185 B2 | 10/2004 | Hasegawa et al. | |
| 7,318,943 B2 | 1/2008 | Baricco et al. | |
| 2001/0043942 A1 | 11/2001 | Hasegawa et al. | |
| 2002/0123648 A1 | 9/2002 | Hasegawa et al. | |
| 2004/0214895 A1 | 10/2004 | Hasegawa et al. | |

FOREIGN PATENT DOCUMENTS

| | | |
|---|---|---|
| EP | 0022361 | 1/1981 |
| EP | 0111628 | 6/1984 |
| EP | 0534865 | 3/1993 |
| EP | 1035109 | 9/2000 |
| EP | 1068804 | 1/2001 |
| FR | 2822396 | 9/2002 |
| GB | 1211062 | 11/1970 |
| WO | WO03/071878 | 9/2003 |

OTHER PUBLICATIONS

International Search Report and Written Opinion for PCT Patent App. No. PCT/EP2009/052259 (Jun. 18, 2009).

* cited by examiner

*Primary Examiner* — Anthony Weier
(74) *Attorney, Agent, or Firm* — Shelly Guest Cermak; Cermak Nakajima LLP

(57) ABSTRACT

The present invention provides a mixed aqueous solution of L-lysine and L-threonine, which is industrially useful as an animal feed ingredient. The solution is stable, concentrated, and has good handleability. Therefore, a mixed aqueous solution of L-lysine and L-threonine is provided which contains L-lysine, L-threonine, and water. The solution has a viscosity of 3300 cp or less at 20° C., a pH of 10-13, and a total concentration of L-lysine and L-threonine in the mixed aqueous solution of 70 g/100 g of water or more.

9 Claims, 3 Drawing Sheets

MIXED AQUEOUS SOLUTION OF L-LYSINE AND L-THREONINE AND METHOD OF PREPARING SAME

This application is a continuation under 35 U.S.C. §120 of PCT Patent Application No. PCT/EP2009/052259, filed Feb. 26, 2009, and of PCT Patent Application No. PCT/IB2008/001889, filed on Feb. 29, 2008, which are incorporated in their entireties by reference.

BACKGROUND OF THE INVENTION

1. Field of the Invention

The present invention relates to a mixed aqueous solution of L-lysine and L-threonine which includes L-lysine, L-threonine, and water, and which can be used as a feed ingredient or the like.

2. Brief Description of the Related Art

An L-lysine based aqueous solution has been reported to be used as a feed ingredient (see EP 111628 B). It has also been reported that when an acid ion, such as a sulfate ion, is added to an L-lysine based aqueous solution, an increase in the solubility of L-lysine, and the absence of precipitated crystals can be obtained (see EP 1035109 B). In addition, it has been reported that by electrodialyzing an L-lysine based aqueous solution to remove counter anions, a highly pure L-lysine base aqueous solution can be obtained (see FR 2822396 B).

Furthermore, it is preferred that products containing amino acids to be used as feed additives be in liquid form, since liquids are more convenient in handling when added to the feed, and uniform mixing can be more easily attained. In fact, amino acids are in liquid form are currently widely used in the feed industry. If the feed is distributed in a liquid form, it is generally preferred that the content of the amino acid be high, which means a lower content of water because of the following reasons: 1) lower transportation cost 2) lower risk of microbial development during the storage of a feed after mixing and 3) more suitable in formulating high nutrient density feed. For example, the L-lysine base aqueous solution is distributed at a concentration slightly below the saturation point to achieve the maximum concentration without risking precipitation of crystals.

Therefore, a liquid feed ingredient containing L-threonine is also desired, but has not been put into practical use yet.

SUMMARY OF THE INVENTION

Since L-threonine has low solubility, unlike L-lysine, a solution containing only L-threonine tends to contain a high amount of water, which results in high transportation costs and a higher risk of microbial contamination. It is an aspect of the invention to provide a mixed aqueous solution of L-lysine and L-threonine with a high total concentration of these two amino acids, which can be prepared, sold, distributed, stored, and used under stable conditions.

It is an aspect of the present invention to provide a mixed aqueous solution of L-lysine and L-threonine comprising L-lysine, L-threonine, and water, wherein said solution has a viscosity of 3300 cp or less at 20° C., a pH of 10-13, and a total concentration of L-lysine and L-threonine of 70 g/100 g of water or more.

It is a further aspect of the present invention to provide the mixed aqueous solution of L-lysine and L-threonine as described above, wherein the concentrations of L-lysine and L-threonine in the mixed aqueous solution are within the region delineated by the L-lysine line, the L-threonine line, the vertical axis, and the horizontal axis in the mutual solubility diagram of L-lysine and L-threonine as measured at 20° C., provided that said region does not include said L-lysine line, L-threonine line, vertical axis, and horizontal axis.

It is a further aspect of the present invention to provide the mixed aqueous solution of L-lysine and L-threonine as described above, wherein the concentrations of L-lysine and L-threonine in the mixed aqueous solution are within the region delineated by the L-lysine line, the L-threonine line, the vertical axis and the horizontal axis in the mutual solubility diagram of L-lysine and L-threonine as measured at −5° C., provided that said region does not include said L-lysine line, L-threonine line, vertical axis, and horizontal axis.

It is a further aspect of the present invention to provide the mixed aqueous solution of L-lysine and L-threonine as described above, which has a viscosity of 2000 cp or less at 20° C.

It is a further aspect of the present invention to provide the mixed aqueous solution of L-lysine and L-threonine as described above, which has a total concentration of L-lysine and L-threonine of 100 g/100 g of water or more.

It is a further aspect of the present invention to provide the mixed aqueous solution of L-lysine and L-threonine as described above, which is prepared using a fermentation solution of L-lysine and/or L-threonine, or a treated solution thereof.

It is a further aspect of the present invention to provide a feed ingredient comprising the mixed aqueous solution of L-lysine and L-threonine as described above.

It is a further aspect of the present invention to provide a method for preparing a mixed aqueous solution of L-lysine and L-threonine comprising L-lysine, L-threonine, and water, said method comprising the step of mixing L-lysine, L-threonine, and water such that the mixed aqueous solution has a viscosity of 3300 cp or less at 20° C., a pH of 10-13, and a total concentration of L-lysine and L-threonine of 70 g/100 g of water or more.

It is another aspect of the present invention to provide a mixed aqueous solution of L-lysine and L-threonine comprising L-lysine, L-threonine, and water, which is prepared by mixing L-lysine, L-threonine, and water such that the mixed aqueous solution has a viscosity of 3300 cp or less at 20° C., a pH of 10-13, and a total concentration of L-lysine and L-threonine of 70 g/100 g of water or more.

According to the present invention, a mixed aqueous solution of L-lysine and L-threonine can be put into practical use, since it is stable, concentrated, easy to handle with low viscosity, and thus can be applied to a compound feed.

DESCRIPTION OF THE PREFERRED EMBODIMENTS

L-lysine and L-threonine can be used as raw materials in an aqueous solution, and can be present in crystal form. Alternatively, a mixed solution of L-lysine and L-threonine, or crystals thereof, can be used. Generally, the origin of the L-lysine or L-threonine is not limited; however, and from the viewpoint of physiological safety or the like, L-lysine and L-threonine can be used as a raw material prepared via fermentation or an enzymatic method, and the amino acids can be purified before use. The purity of the L-lysine raw material can be 95% or more in dry matter weight, while the purity of the L-threonine raw material can be 98.5% or more in dry matter. In addition, these L-amino acid raw materials can contain minerals such as potassium, magnesium, calcium, etc., but the total amount of minerals can be 2400 ppm or less. This is so that the risk of precipitation of the minerals can be minimized. The mixed solution of L-lysine and L-threonine can be generally used at the temperature range of −5 to 60° C. Those skilled in the art can determine said temperature for the product considering the manufacturing temperature, the temperature of the area where the product is sold and distributed, the storage temperature and operating temperature, so that the mixed solution is maintained in a stable state in which insoluble substances such as crystals do not precipitate. If necessary, a storage tank with an insulating jacket can be used to avoid the precipitation. Generally, the mixed solution is distributed and used at a temperature between −5° C. and ambient temperature, such as around 20° C., and use at −5° C. or less is not useful due to potential precipitation of crystals. Furthermore, use at 60° C. or more is also not useful due to the potential generation of decomposed material by an amino-carbonyl reaction. This reaction can occur especially if raw materials prepared using a fermentation method or an enzymatic method are used. Finally, if the mixed solution saturated with L-lysine and L-threonine at −5° C. is heated to a higher temperature, insoluble substances such as crystals will not precipitate.

Figure 3:
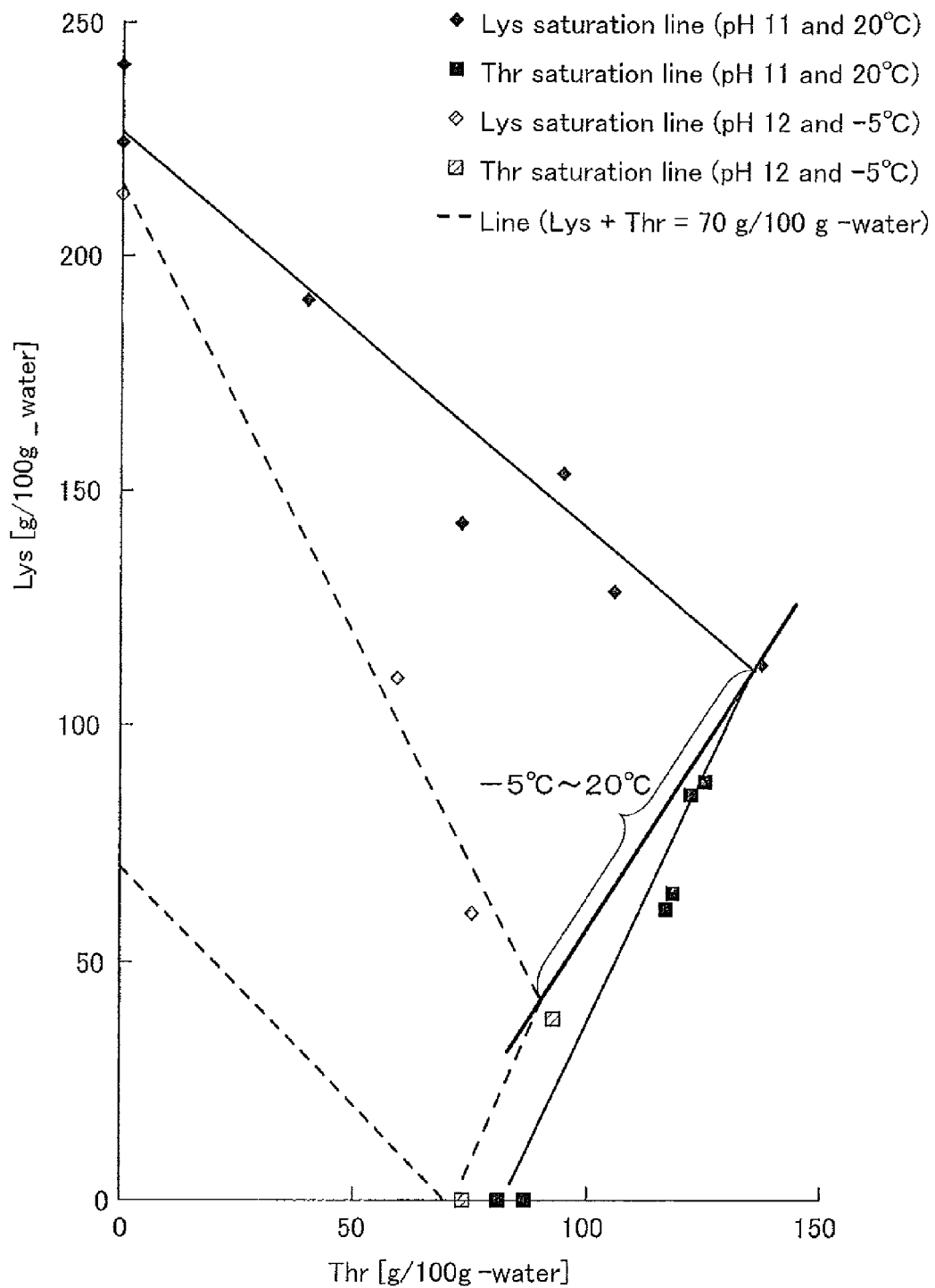
FIG. 3 shows temperature dependences of mutual solubility of L-lysine and L-threonine.

As mentioned above, although the mixed solution of L-lysine and L-threonine can be generally used in the range of −5 to 60° C., the mutual solubility value of the mixed solution saturated with both L-lysine and L-threonine increases with an increase of temperature. In connection to this, the mutual solubility values at the temperature between −5° C. and 20° C. can be estimated as shown in FIG. 3. Since pH 11.3 (20° C.) and pH 12 (−5° C.) are so close, these pH values were considered as being the same when preparing FIG. 3.

The pH range of the mixed solution of L-lysine and L-threonine can be restricted to from 10 to 13. A pH of less than 10 is not useful because of the low solubility of L-threonine, and a pH of more than 13 is not useful because of the handling difficulty when using the mixed solution as a feed ingredient (i.e. it is designated as a hazardous material). Although a pH variation between 10 and 13 can be accompanied by a mutual solubility variation and a viscosity variation, the mutual solubility diagram can be easily prepared according to the described method.

In order to control the pH, if alkali is added to the solution, an alkali metal or alkaline earth metal, such as caustic soda, caustic potash, or the like, can be used, and if acid is added to the solution, sulfuric acid, acetic acid, or the like can be used.

The total concentration of L-lysine and L-threonine in the mixed aqueous solution can be 70 g/100 g of water or more, which can result in a feed solution containing a high level of L-lysine and L-threonine.

As described below, it has been found that in the mixed solution of L-lysine and L-threonine, the viscosity of the solution can change significantly depending on whether or not the L-lysine concentration is higher than the L-lysine saturation line (see the Figures). In the mixed solution, from the viewpoint of workability and the like, the viscosity of the solution can be, at 20° C., 3300 cp or less, and in another example, 3000 cp or less. In addition, from the viewpoint of distribution, storage, and the like, the viscosity of the solution can be, at −5° C., 3300 cp or less, and in another example, 3000 cp or less. That is, by maintaining the viscosity of the mixed solution at 3000 cp or less, the stability of the mixed solution during distribution and storage can be easily increased. Therefore, 3300 cp or less is one example, and 3000 cp or less is another example.

Figure 1:
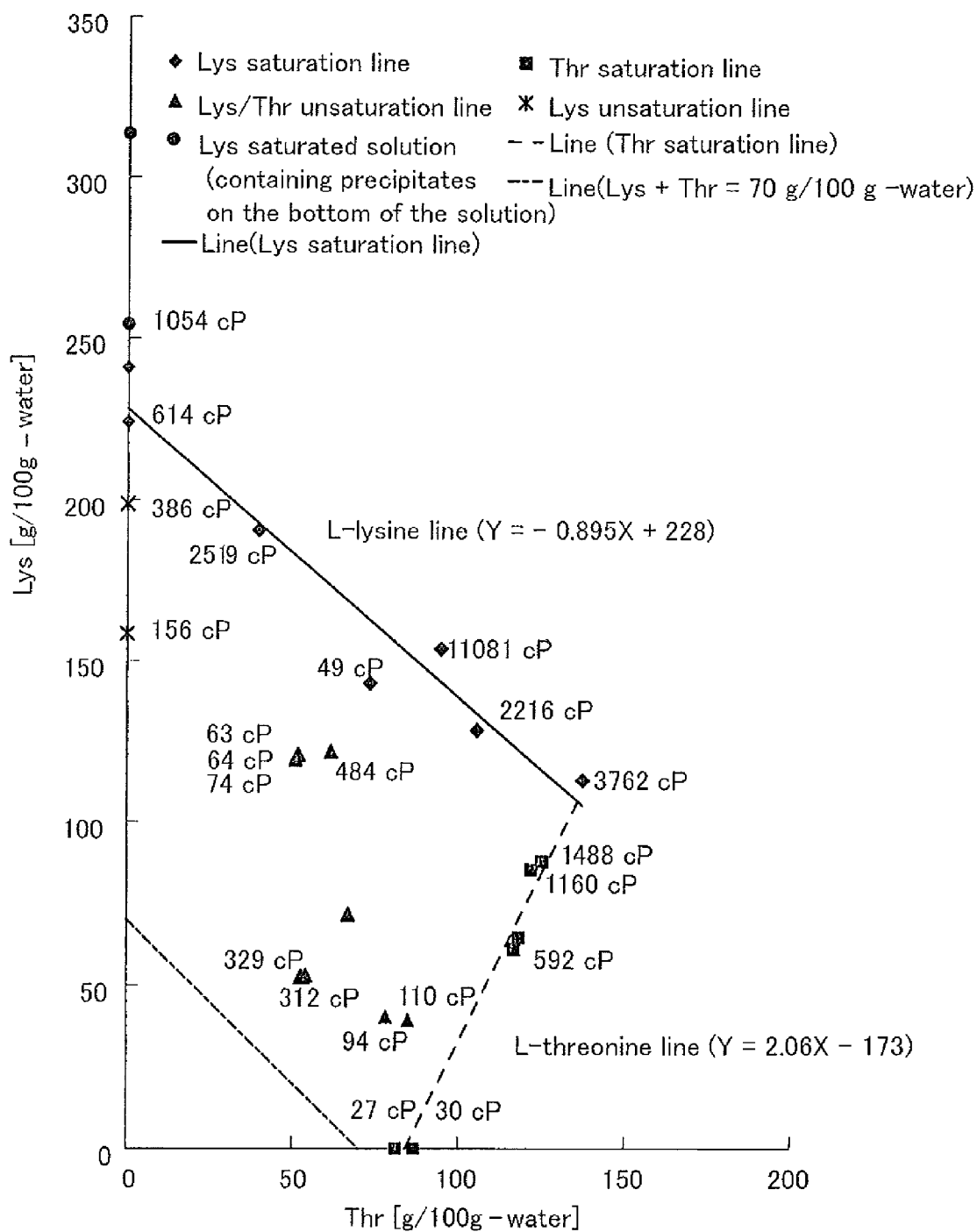
FIG. 1 shows a mutual solubility diagram of L-lysine and L-threonine at 20° C. and pH 11.3.

An example of a mutual solubility diagram at room temperature is shown in FIG. 1, which pertains to Example 1. The L-lysine line can be specified as $Y=0.895X+228$, and the L-threonine line can be specified as $Y=2.06X-173$, at 20° C. and pH 11.3.

An example of a mixed solution is 191 g/100 g of water of L-lysine and 40 g/100 g of water of L-threonine. These concentrations are slightly less than the L-lysine line, and as a result, crystals do not precipitate. This solution has a viscosity of 2519 cp, is stable, and has an excellent handleability.

Alternatively, a mixed solution containing 154 g/100 g of water of L-lysine and 95 g/100 g of water of L-threonine, which are above the L-lysine line, results in precipitated crystals containing L-lysine and a viscosity reaching up to 11081 cp. A solution with this viscosity is actually a gel and completely uncontrollable.

Figure 2:
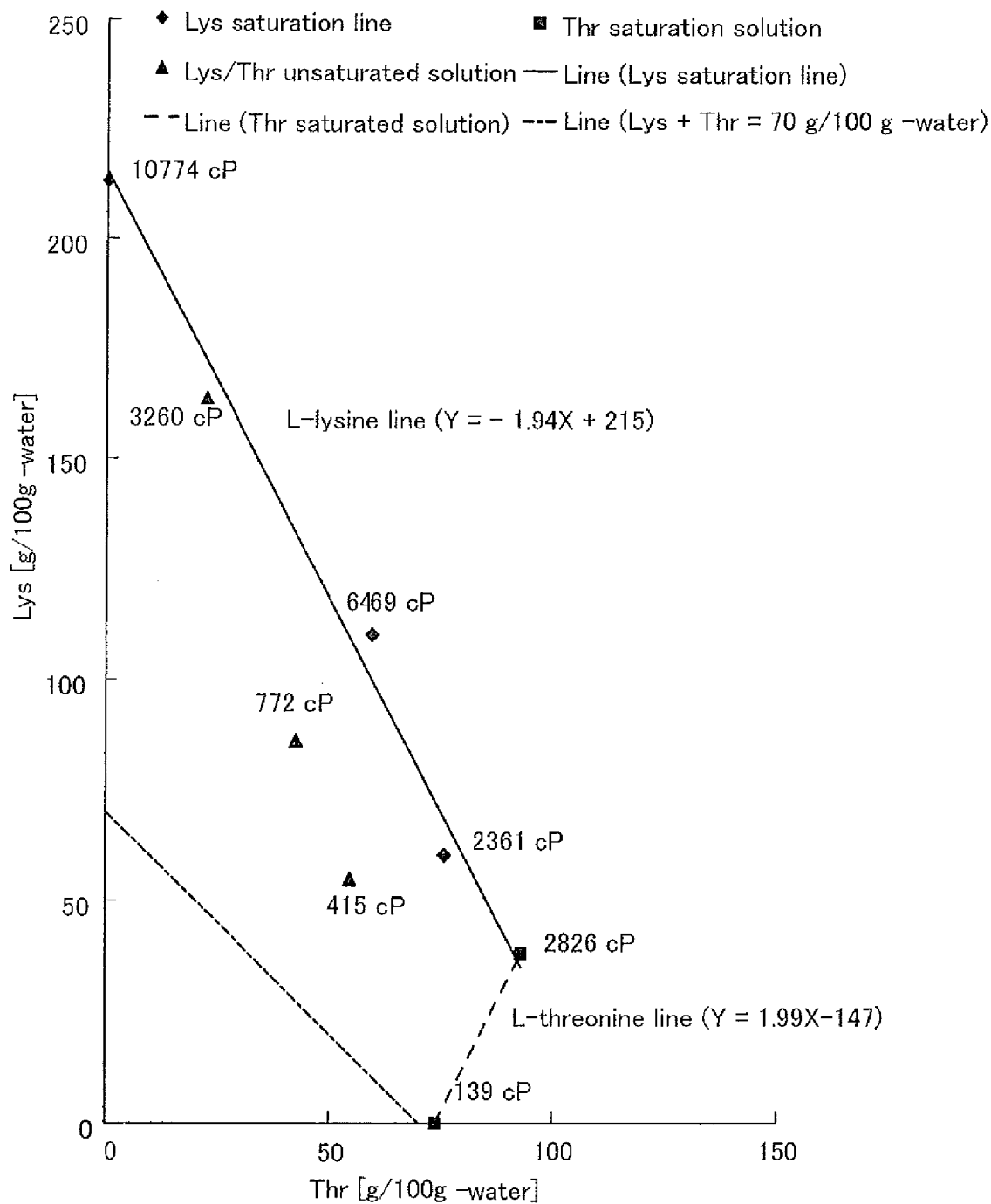
FIG. 2 shows a mutual solubility diagram of L-lysine and L-threonine at −5° C. and pH 12.

An example of a mutual solubility diagram at a lower temperature is shown in FIG. 2, which pertains to Example 2. The L-lysine line can be specified as $Y=-1.94X+215$, and the L-threonine line can be specified as $Y=1.99X-147$, at −5° C. and pH 12.

An example of a mixed solution includes one with 60 g/100 g of water of L-lysine and 76 g/100 g of water of L-threonine. These concentrations are slightly less than the L-lysine line, and as a result, crystals do not precipitate. This solution has a viscosity of 2361 cp, is stable, and has excellent handleability at −5° C.

Alternatively, a mixed solution containing 110 g/100 g of water of L-lysine and 60 g/100 g of water of L-threonine, which are above the L-lysine line, results in precipitated crystals containing L-lysine and a viscosity reaching up to 6469 cp. A solution with this viscosity is actually a gel, and is completely uncontrollable.

To the right of the L-threonine line, the solution contains a large amount of L-threonine, and L-threonine crystals will precipitate and fall to the bottom of the solution.

Furthermore, so the solution is easy to handle and spray when mixed with feed, the viscosity of the mixed solution can be 2000 cp or less at a specific temperature between −5° C. and 60° C., for example 60° C., and in particular 20° C.

In addition, to reduce the content of water so that the transportation costs and the risk of microbial contamination is lower during the storage of a feed after mixing, as well as enabling the formulation of a high nutrient density feed, the total concentration of L-lysine and L-threonine can be 100 g/100 g of water or more in the mixed aqueous solution.

The mutual solubility diagrams can be determined as follows.

The L-threonine is added into a saturated solution of L-lysine at a predetermined pH and temperature, or the L-lysine is added into a saturated solution of L-threonine at a predetermined pH and temperature. In addition, the mixed aqueous solution of L-lysine and L-threonine having various concentrations of L-lysine and L-threonine prepared at a predetermined pH and temperature to precipitate crystals can be concentrated or cooled. The resulting crystals are separated from the mother liquor, and then a solubility diagram is plotted setting the concentration of L-lysine in the mother liquor on the horizontal axis and the concentration of L-threonine in the mother liquor on the vertical axis. A line is obtained using linear approximation of saturation points at which gelatinous L-lysine is precipitated, and is defined as the "L-lysine line". The line obtained using linear approximation of saturation points at which needle-shaped L-threonine is precipitated is defined as the "L-threonine line" in the mutual solubility diagram. Data of the mutual solubility at pH 11.3 and 20° C., and at pH 12 and −5° C. are shown in the following tables.

TABLE 1 the mutual solubility of L-lysine and L-threonine at pH 11.3 and 20° C.

| No. | Lys [g/100 g of water] | Thr [g/100 g of water] | Remarks |
|---|---|---|---|
| 1 | 241 | 0 | Lys line |
| 2 | 224 | 0 | |
| 3 | 191 | 40 | |
| 4 | 143 | 73 | |
| 5 | 154 | 95 | |
| 6 | 129 | 106 | |
| 7 | 113 | 137 | |
| 8 | 0 | 81 | Thr line |
| 9 | 0 | 87 | |
| 10 | 61 | 117 | |
| 11 | 64 | 118 | |
| 12 | 85 | 122 | |
| 13 | 88 | 125 | |

TABLE 2 the mutual solubility of L-lysine and L-threonine at pH 12 and −5° C.

| No. | Lys [g/100 g of water] | Thr [g/100 g of water] | Remarks |
|---|---|---|---|
| 1 | 213 | 0 | Lys line |
| 2 | 110 | 60 | |
| 3 | 60 | 76 | |
| 4 | 0 | 74 | Thr line |
| 5 | 38 | 93 | |

In accordance with the above mutual solubility diagram, and considering the handleability, the total concentration of L-lysine and L-threonine can be 70 g/100 g of water or more, and in another example, 100 g/100 g of water or more.

The viscosity was measured using a rotational viscometer (Rheomat RM 180, Metller Toledo) and the measuring system DIN 53019 was used to measure saturated solutions of L-lysine containing L-threonine at the predetermined concentrations, saturated solutions of L-threonine containing L-lysine at the predetermined concentrations, and mixed solutions of L-lysine and L-threonine at the predetermined concentrations. Data of the mixed solutions at pH 11.3 and 20° C., and pH 12 and −5° C. are shown in the following tables.

TABLE 3 the viscosity of the mixed solutions of L-lysine and L-threonine at pH 11.3 and 20° C.

| No. | Lys [g/100 g of water] | Thr [g/100 g of water] | Viscosity [cp] |
|---|---|---|---|
| 1 | 224 | 0 | 614 |
| 2 | 191 | 40 | 2519 |
| 3 | 143 | 73 | 49 |
| 4 | 154 | 95 | 11081 |
| 5 | 129 | 106 | 2216 |
| 6 | 113 | 137 | 3762 |
| 7 | 0 | 81 | 27 |
| 8 | 0 | 87 | 30 |
| 9 | 61 | 117 | 592 |
| 10 | 85 | 122 | 1160 |

TABLE 3-continued the viscosity of the mixed solutions of L-lysine and L-threonine at pH 11.3 and 20° C.

| No. | Lys [g/100 g of water] | Thr [g/100 g of water] | Viscosity [cp] |
|---|---|---|---|
| 11 | 88 | 125 | 1488 |
| 13 | 53 | 54 | 63 |
| 14 | 53 | 53 | 64 |
| 15 | 53 | 53 | 74 |
| 17 | 40 | 78 | 94 |
| 18 | 39 | 85 | 110 |
| 19 | 121 | 52 | 312 |
| 20 | 120 | 51 | 329 |
| 21 | 122 | 61 | 484 |
| 22 | 158 | 0 | 156 |
| 23 | 199 | 0 | 386 |
| 24 | 254 | 0 | 1054 |

TABLE 4 the viscosity of the mixed solutions of L-lysine and L-threonine at pH 12 and −5° C.

| No. | Lys [g/100 g of water] | Thr [g/100 g of water] | Viscosity [cp] |
|---|---|---|---|
| 1 | 213 | 0 | 10774 |
| 2 | 110 | 60 | 6469 |
| 3 | 60 | 76 | 2361 |
| 4 | 0 | 74 | 139 |
| 5 | 38 | 93 | 2826 |
| 6 | 55 | 55 | 415 |
| 7 | 86 | 43 | 772 |
| 8 | 164 | 22 | 3260 |

Thus, since the mutual solubility can be identified, the mixed aqueous solution of L-lysine and L-threonine having a viscosity of 3300 cp or less can be obtained if the pH is between 10 to 13, and the total concentration of L-lysine and L-threonine is determined to be 70 g/100 g of water or more, and the concentration of L-threonine is determined to be the specific concentration within the area of the mutual solubility.

The mixed aqueous solution of L-lysine and L-threonine can be used as an animal feed ingredient.

A solution prepared using an appropriate mix ratio of L-lysine and L-threonine (for example, 25 wt. % of L-threonine and 25 wt. % of L-lysine) can be added in the amount of about 1 to 5 kg into one ton of animal feed using a spray nozzle. Because the required amino acids can be accurately and easily added into animal feed with a single mixing, it is more useful than an aqueous solution or granulated dry crystals containing L-lysine or L-threonine alone.

The present invention will be explained in more detail with reference to the following specific and non-limiting Examples in which the analysis of L-lysine and L-threonine was made by AOAC official method 999.13 (AOAC Official Methods of Analysis (2005)—Animal feed, Chapter 4, p 20-24).

EXAMPLES

Example 1

Example at 20° C. and pH 11.3

763.69 g of 50% L-lysine solution and 50.12 g of L-threonine crystal, which were obtained from a commercial source (Ajinomoto Eurolysine S. A. S., (50% L-lysine; Lot 6256), (L-threonine; Lot 6255)), were mixed in a 1 liter glass beaker.

61.83 g of 50% caustic soda (solid sodium hydroxide; Merck KGaA, reagent grade (purity>99%)) was then added to adjust the pH to 11 at room temperature. This solution was concentrated about 1.6 fold by using a rotary evaporator (pressure: 100 mbar, water bath temperature: 60° C.). As a result, precipitation of crystals was observed. The slurry was stirred overnight at room temperature (20° C.) so that the saturated solution does not become super saturated. Then, the saturated solution and crystals were separated at 20° C. by centrifugation at 4000 rpm for 30 min (J2-21M/E-Beckman, rotor JA-14). The viscosity and the amounts of L-lysine, L-threonine, sodium, and water in the saturated solution were measured by analysis under the following conditions:

L-lysine content: Amino Acid Analyzer AMINOTAC JLC-500/V (JEOL)

L-threonine content: Amino Acid Analyzer AMINOTAC JLC-500/V (JEOL)

Viscosity: a rotational viscometer (Rheomat RM 180, Mettler Toledo) and the measure system DIN 53019

Sodium content: Ion Chromatography DX320 (DIONEX)

Water content: Drying in the oven at 105° C. overnight

Then, the L-lysine and L-threonine content in the saturated solution were plotted on the graph. There are three regions in which crystals precipitated in the saturated solution: the region containing L-lysine alone, the region containing both L-lysine and L-threonine, and the region containing L-threonine alone. If separated crystals corresponding to the saturated solution were determined as L-lysine, these plots were defined as the "he parated crystals correspt line. And if separated crystals corresponding to the saturated solution were determined as L-threonine, these plots were defined as the "L-threonine line" on a straight line.

Example 2

Example at −5° C. and pH 12

514.20 g of L-lysine solution, which had a L-lysine concentration of 61.46% and a pH which was adjusted to 10.98 at 20° C., and 441.79 g of a L-threonine solution, which had L-threonine concentration of 42.93% and a pH which was adjusted to 11.02 at 20° C., were mixed in a 1 liter glass beaker. Both the 61.46% L-lysine solution (50% L-lysine; Lot 6256) and the 42.93% L-threonine solution (L-threonine; Lot 7158) were obtained from a commercial source (Ajinomoto Eurolysine S. A. S.) after evaporation using a rotary evaporator (pressure: 100 mbar, water bath temperature: 60° C. The resulting solution mixed from L-lysine and L-threonine was stirred at room temperature overnight and cooled down to −5° C. The solution was maintained at −5° C. under agitation for 48 hours, and then under static conditions overnight. As a result, precipitation of crystals was observed. Then, the saturated solution and crystals were separated at −5° C. by centrifugation at 4000 rpm for 30 min (J2-21M/E-Beckman, rotor JA-14). The viscosity and the amounts of L-lysine, L-threonine, sodium, and water in saturated solution were measured by analysis under the following conditions:

L-lysine content: Amino Acid Analyzer AMINOTAC JLC-500/V (JEOL)

L-threonine content: Amino Acid Analyzer AMINOTAC JLC-500/V (JEOL)

Viscosity: a rotational viscometer (Rheomat RM 180, Mettler Toledo) and the measure system DIN 53019

Sodium content: Ion Chromatography DX320 (DIONEX)

Water content: Drying in the oven at 105° C. overnight

Then, the L-lysine and L-threonine contents in the saturated solution were plotted on the graph. There are three regions in which crystals precipitated in the saturated solution: the region containing L-lysine alone, the region containing both L-lysine and L-threonine, and the region containing L-threonine alone. If separated crystals corresponding to the saturated solution were determined as L-lysine by gel, these plots were defined as the "he region containing L-threonine alone. If separated crystals corresponding to the saturated solution were determined as L-threonine by needle-like crystals, these plots were defined as the "L-threonine line" on a straight line.

INDUSTRIAL APPLICABILITY

The present invention is a mixed aqueous solution of L-lysine and L-threonine which is stable and concentrated and which has good handleability and thus can be used as an animal feed ingredient.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A mixed aqueous solution of L-lysine and L-threonine comprising L-lysine, L-threonine and water, wherein said solution has a viscosity of 3300 cp or less at 20° C., a pH of 10-13, and wherein said solution contains L-lysine in the amount of at least 38 g/100 g water and L-threonine in the amount of at least 22 g/100 g of water.

2. The mixed aqueous solution of L-lysine and L-threonine according to claim 1, wherein the concentrations of L-lysine and L-threonine in the mixed aqueous solution are within the region delineated by the L-lysine line, the L-threonine line, the vertical axis, and the horizontal axis in the mutual solubility diagram of L-lysine and L-threonine as measured at 20° C., as shown in FIG. 1, provided that said region does not include said L-lysine line, L-threonine line, vertical axis and horizontal axis.

3. The mixed aqueous solution of L-lysine and L-threonine according to claim 1, wherein the concentrations of L-lysine and L-threonine in the mixed aqueous solution are within the region delineated by the L-lysine line, the L-threonine line, the vertical axis and the horizontal axis in the mutual solubility diagram of L-lysine and L-threonine as measured at −5° C. as shown in FIG. 2, provided that said region does not include said L-lysine line, L-threonine line, vertical axis and horizontal axis.

4. The mixed aqueous solution of L-lysine and L-threonine according to claim 1, which has a viscosity of 2000 cp or less at 20° C.

5. The mixed aqueous solution of L-lysine and L-threonine according to claim 1, which has a total concentration of L-lysine and L-threonine of 100 g/100 g of water or more.

6. The mixed aqueous solution of L-lysine and L-threonine according to claim 1, which is prepared using a fermentation solution of L-lysine and/or L-threonine, or a treated solution thereof.

7. A feed ingredient comprising the mixed aqueous solution of L-lysine and L-threonine according to claim 1.

8. A method for preparing a mixed aqueous solution of L-lysine and L-threonine comprising L-lysine, L-threonine, and water, said method comprising the step of mixing L-lysine, L-threonine, and water such that the mixed aqueous solution has a viscosity of 3300 cp or less at 20° C., a pH of 10-13, and wherein said solution contains L-lysine in the amount of at least 38 g/100 g water and L-threonine in the amount of at least 22 g/100 g of water.

9. A mixed aqueous solution of L-lysine and L-threonine comprising L-lysine, L-threonine, and water, which is prepared by mixing L-lysine, L-threonine and water such that the mixed aqueous solution has a viscosity of 3300 cp or less at 20° C., a pH of 10-13 and wherein said solution contains L-lysine in the amount of at least 38 g/100 g water and L-threonine in the amount of at least 22 g/100 g of water.

* * * * *